United States Patent
Hashida et al.

(10) Patent No.: US 9,175,586 B2
(45) Date of Patent: Nov. 3, 2015

(54) CONTROL APPARATUS AND CONTROL METHOD FOR INTERNAL COMBUSTION ENGINE

(75) Inventors: Tatsuhiro Hashida, Susono (JP); Hiroki Nishijima, Shizyoka-ken (JP)

(73) Assignee: TOYOTA JIDOSHA KABUSHIKI KAISHA, Aichi-ken (JP)

(*) Notice: Subject to any disclaimer, the term of this patent is extended or adjusted under 35 U.S.C. 154(b) by 0 days.

(21) Appl. No.: 14/358,161

(22) PCT Filed: Nov. 15, 2011

(86) PCT No.: PCT/JP2011/076284
§ 371 (c)(1),
(2), (4) Date: May 14, 2014

(87) PCT Pub. No.: WO2013/073006
PCT Pub. Date: May 23, 2013

(65) Prior Publication Data
US 2014/0311129 A1   Oct. 23, 2014

(51) Int. Cl.
| | |
|---|---|
| *F01N 3/00* | (2006.01) |
| *F01N 3/021* | (2006.01) |
| *F02D 41/14* | (2006.01) |
| *F02D 41/22* | (2006.01) |
| *G01N 15/06* | (2006.01) |
| *G01N 15/00* | (2006.01) |

(52) U.S. Cl.
CPC ............ *F01N 3/021* (2013.01); *F02D 41/1466* (2013.01); *F02D 41/1494* (2013.01); *F02D 41/222* (2013.01); *G01N 15/0606* (2013.01); *G01N 15/0656* (2013.01); *F01N 2560/05* (2013.01); *F01N 2560/20* (2013.01); *F01N 2900/0416* (2013.01); *G01N 2015/0046* (2013.01); *Y02T 10/20* (2013.01); *Y02T 10/40* (2013.01)

(58) Field of Classification Search
USPC ............ 60/274, 276, 277, 286, 295, 297, 311
See application file for complete search history.

(56) References Cited

U.S. PATENT DOCUMENTS

| | | | |
|---|---|---|---|
| 6,947,831 B2 * | 9/2005 | van Nieuwstadt | 701/114 |
| 8,136,343 B2 * | 3/2012 | Zawacki et al. | 60/276 |
| 8,261,540 B2 * | 9/2012 | Konstandopoulos et al. | 60/297 |
| 8,845,783 B2 * | 9/2014 | Takaoka et al. | 95/26 |
| 8,915,119 B2 * | 12/2014 | Ueno et al. | 73/23.33 |
| 8,943,809 B2 * | 2/2015 | Aoki et al. | 60/295 |
| 2011/0048106 A1 | 3/2011 | Zawacki et al. | |

FOREIGN PATENT DOCUMENTS

JP 2009-144577 A   7/2009

* cited by examiner

*Primary Examiner* — Binh Q Tran
(74) *Attorney, Agent, or Firm* — Sughrue Mion, PLLC

(57) ABSTRACT

By raising a temperature of an element portion of a particulate matter sensor (8) that is arranged in an exhaust passage (4) of an internal combustion engine (2), a heat generation amount that results from the combustion of particulate matters is detected, during a removal treatment of removing, through combustion, particulate matters that are deposited on the element portion. Besides, an amount of particulate matters that are deposited on the element portion of the particulate matter sensor (8) is detected on the basis of an output of the particulate matter sensor (8), before the start of this removal treatment. On the other hand, an amount of particulate matters that are deposited on the element portion before the start of the removal treatment is detected in accordance with the heat generation amount. Furthermore, it is determined whether or not there is an abnormality in the particulate matter sensor (8), on the basis of a difference between a first particulate matter amount that is detected on the basis of the output of the particulate matter sensor (8) and a second particulate matter amount that is detected on the basis of the heat generation amount.

7 Claims, 4 Drawing Sheets

CONTROL APPARATUS AND CONTROL METHOD FOR INTERNAL COMBUSTION ENGINE

TECHNICAL FIELD

This invention relates to a control apparatus and a control method for an internal combustion engine. More concretely, this invention relates to a control apparatus and a control method for controlling an internal combustion engine that has an exhaust passage in which a particulate matter sensor is arranged.

BACKGROUND ART

For example, in a system of Patent Document 1, a particulate matter sensor (a PM sensor) for detecting particulate matters (hereinafter referred to also as "PM") in an exhaust passage of an internal combustion engine is arranged. This PM sensor includes an insulating substrate, and a pair of electrodes that are arranged, spaced apart from each other, on the insulating substrate.

If the PM in exhaust gas is deposited between the pair of the electrodes of this PM sensor, the conductivity between the electrodes changes. There is a certain correlation between the amount of the deposited PM and the conductivity between the electrodes, and the resistance between the electrodes changes in accordance with the amount of the PM deposited between the electrodes. Besides, there is a correlation between the amount of the PM deposited between the electrodes and the amount of the PM in exhaust gas. Accordingly, the amount of the PM in exhaust gas is detected by detecting a resistance value between the electrodes of the PM sensor.

By the way, in the art of Patent Document 1, the PM sensor is arranged downstream of a particulate matter collection filter (a diesel particulate filter; hereinafter referred to also as "a DPF"). In Patent Document 1, it is determined whether or not there is a malfunction in the DPF, by detecting an amount of the PM discharged downstream of the DPF on the basis of the resistance value between the electrodes of the PM sensor.

RELATED ART DOCUMENT

Patent Document

Patent Document 1: Japanese Patent Application Publication No. 2009-144577 (JP-2009-144577 A)

SUMMARY OF THE INVENTION

Problem to be Solved by the Invention

The PM sensor is exposed to high-temperature exhaust gas, and is used with a high voltage applied thereto. Thus, for example, the evaporation of the electrodes, the adhesion of insulating materials such as Ash and the like to the electrodes, a change in the clearance between the electrodes through migration, and the like may be caused. As a result, the resistance between the electrodes of the PM sensor changes, and the correlation between the amount of PM and the resistance value breaks. It is conceivable that the PM sensor assume a state of failing to issue a correct output corresponding to the amount of PM. In the case where the output of the PM sensor deviates, there may occur a situation in which the accuracy of the control based on the output of the PM sensor deteriorates, for example, an incorrect determination is made on the presence or absence of a malfunction or the like, in making a determination on a malfunction in the DPF.

It is an object of the invention to solve the aforementioned problem. The invention provides a control apparatus and a control method for an internal combustion engine that are improved so as to detect an abnormality resulting from a deterioration in a PM sensor and perform control with higher accuracy on the basis of an output of the PM sensor.

Means for Solving the Problem

In order to achieve the aforementioned object, the first invention provides a control apparatus for an internal combustion engine that includes means for carrying out a removal treatment of removing, through combustion, particulate matters deposited on an element portion of a particulate matter sensor that is arranged in an exhaust passage of the internal combustion engine, by raising a temperature of the element portion, and means for detecting a heat generation amount that results from combustion of the particulate matters during the removal treatment. Besides, this control apparatus for the internal combustion engine includes first detection means and second detection means, which detect an amount of particulate matters. The first detection means detects an amount of particulate matters deposited on the element portion of the particulate matter sensor, on the basis of an output of the particulate matter sensor before the start of the removal treatment. The second detection means detects an amount of particulate matters that are deposited on the element portion before the start of the removal treatment, in accordance with the heat generation amount. Furthermore, this control apparatus for the internal combustion engine includes abnormality determination means for determining whether or not there is an abnormality in the particulate matter sensor, on the basis of a difference between a first particulate matter amount detected by the first detection means and a second particulate matter amount detected by the second detection means.

The second invention modifies the first invention as follows. In the second invention, the control apparatus for the internal combustion engine further includes means for prohibiting the start of the removal treatment until a temperature of exhaust gas of the internal combustion engine becomes lower than a reference temperature.

The third invention modifies the first or second invention as follows. In the third invention, the control apparatus for the internal combustion engine further includes means for prohibiting the start of the removal treatment until the amount of particulate matters deposited on the element portion reaches a reference amount.

The fourth invention modifies any one of the first to third inventions as follows. In the fourth invention, a particulate matter collection filter for collecting the particulate matters is arranged in the exhaust passage upstream of the particulate matter sensor. The control apparatus for the internal combustion engine according to the fourth invention further includes means for determining, on the basis of an output of the particulate matter sensor, whether or not there is a malfunction in the particulate matter collection filter, and timing setting means for setting a detection timing for detecting an output of the particulate matter sensor, for determining whether or not there is a malfunction in the particulate matter collection filter. The timing setting means sets the detection timing later than a detection timing in a case where it is determined that the particulate matter sensor is normal, if it is determined that the particulate matter sensor is abnormal and the first particulate matter amount is smaller than the second particulate matter amount. On the other hand, the timing setting means sets the detection timing earlier than the detection timing in the case where it is determined that the particulate matter sensor is normal, if it is determined that the particulate matter sensor is abnormal and the first particulate matter amount is larger than the second particulate matter amount.

The fifth invention modifies any one of the first to third inventions as follows. In the fifth invention, a particulate matter collection filter for collecting the particulate matters is arranged in the exhaust passage upstream of the particulate matter sensor. The control apparatus for the internal combustion engine according to the fifth invention includes means for determining, on the basis of an output of the particulate matter sensor, whether or not there is a malfunction in the particulate matter collection filter, and voltage setting means for setting a magnitude of a particulate matter collection voltage that is applied to the particulate matter sensor, in determining whether or not there is a malfunction in the particulate matter collection filter. The voltage setting means sets the particulate matter collection voltage larger than a particulate matter collection voltage that is applied in a case where it is determined that the particulate matter sensor is normal, if it is determined that the particulate matter sensor is abnormal and the first particulate matter amount is smaller than the second particulate matter amount. On the other hand, the voltage setting means sets the particulate matter collection voltage smaller than the particulate matter collection voltage that is applied in the case where it is determined that the particulate matter sensor is normal, if it is determined that the particulate matter sensor is abnormal and the first particulate matter amount is larger than the second particulate matter amount.

The sixth invention provides a control method for an internal combustion engine that includes a process of carrying out a removal treatment of removing, through combustion, particulate matters deposited on an element portion of a particulate matter sensor that is arranged in an exhaust passage of the internal combustion engine, by raising a temperature of the element portion, and a process of detecting a heat generation amount that results from the combustion of the particulate matters during the removal treatment. Besides, this control method for the internal combustion engine includes a first detection process and a second detection process, in which an amount of particulate matters is detected. In the first detection process, an amount of particulate matters deposited on the element portion of the particulate matter sensor is detected, on the basis of an output of the particulate matter sensor before the start of the removal treatment. On the other hand, in the second detection process, an amount of particulate matters that are deposited on the element portion before the start of the removal treatment is detected in accordance with the heat generation amount. Furthermore, this control method includes an abnormality determination process of determining whether or not there is an abnormality in the particulate matter sensor, on the basis of a difference between a first particulate matter amount detected in the first detection process and a second particulate matter amount detected in the second detection process.

The seventh invention modifies the sixth invention as follows. In the seventh invention, the start of the removal treatment is prohibited until a temperature of exhaust gas of the internal combustion engine becomes lower than a reference temperature.

The eighth invention modifies the sixth or seventh invention as follows. In the eighth invention, the start of the removal treatment is prohibited until the amount of particulate matters deposited on the element portion reaches a reference amount.

The ninth invention modifies any one of the sixth to eighth inventions as follows. In the ninth invention, a particulate matter collection filter for collecting the particulate matters is arranged in the exhaust passage of the internal combustion engine upstream of the particulate matter sensor. This control method for the internal combustion engine further includes a process of determining, on the basis of an output of the particulate matter sensor, whether or not there is a malfunction in the particulate matter collection filter. A detection timing for detecting an output of the particulate matter sensor for determining whether or not there is a malfunction in the particulate matter collection filter is set later than a detection timing in a case where it is determined that the particulate matter sensor is normal, if it is determined that the particulate matter sensor is abnormal and the first particulate matter amount is smaller than the second particulate matter amount. On the other hand, the detection timing is set earlier than the detection timing in the case where it is determined that the particulate matter sensor is normal, if it is determined that the particulate matter sensor is abnormal and the first particulate matter amount is larger than the second particulate matter amount.

The tenth invention modifies any one of the sixth to eighth inventions as follows. In the tenth invention, a particulate matter collection filter for collecting the particulates is arranged in the exhaust passage of the internal combustion engine upstream of the particulate matter sensor. This control method for the internal combustion engine further includes a process of determining, on the basis of an output of the particulate matter sensor, whether or not there is a malfunction in the particulate matter collection filter. A magnitude of a particulate matter collection voltage that is applied to the particulate matter sensor in determining whether or not there is a malfunction in the particulate matter collection filter is set larger than a particulate matter collection voltage that is applied in a case where it is determined that the particulate matter sensor is normal, if it is determined that the particulate matter sensor is abnormal and the first particulate matter amount is smaller than the second particulate matter amount. On the other hand, the magnitude of the particulate matter collection voltage is set smaller than the particulate matter collection voltage that is applied in the case where it is determined that the particulate matter sensor is normal, if it is determined that the particulate matter sensor is abnormal and the first particulate matter amount is larger than the second particulate matter amount.

Effects of the Invention

According to this invention, the amount of particulate matters that are deposited on the element portion before the start of the removal treatment of particulate matters can be detected on the basis of each of the sensor output before the start of the removal treatment of particulate matters and the heat generation amount during the removal treatment. Then, by comparing the first particulate matter amount based on the sensor output and the second particulate matter amount based on the heat generation amount with each other, it can be confirmed whether or not the output of the particulate matter sensor is normal, and it can be determined whether or not there is an abnormality in the particulate matter sensor.

Besides, as is the case with the second, third, seventh and eighth inventions, by prohibiting the start of the removal treatment of particulate matters until a predetermined condition is fulfilled, the heat generation amount that results from the removal treatment of particulate matters can be more accurately detected. Accordingly, the second particulate matter amount can be more accurately obtained, and it can be determined with high accuracy whether or not there is an abnormality in the particulate matter sensor.

Besides, as is the case with the fourth, fifth, ninth and tenth inventions, as for the configuration in which the detection timing or the applied voltage is changed through a comparison between the first particulate matter amount and the second particulate matter amount if it is determined that the particulate matter sensor is abnormal, even in the case where there is an abnormality in the particulate matter sensor, a state corresponding to a change in the output sensitivity thereof can be realized, and a more or less accurate determination can be made on a malfunction in the particulate matter collection filter.

MODES FOR CARRYING OUT THE INVENTION

The embodiments of the invention will be described hereinafter with reference to the drawings. Incidentally, in the respective drawings, like or equivalent components are denoted by like reference symbols, and the description thereof is simplified or omitted.

First Embodiment

[About Overall Configuration of System of this First Embodiment]

Figure 1:
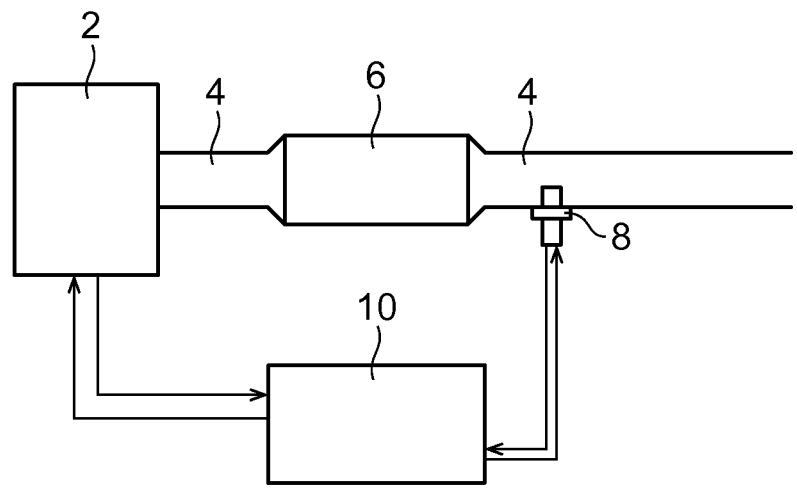
FIG. 1 is a schematic view for illustrating an overall configuration of a system in each embodiment of the invention.

FIG. 1 is a view for illustrating an overall configuration of a system of the first embodiment of this invention. A system of FIG. 1 is used by being mounted in a vehicle or the like. In the system shown in FIG. 1, a diesel particulate filter (a DPF) 6 as a particulate matter collection filter is installed in an exhaust passage 4 of an internal combustion engine 2. The DPF 6 is a filter that collects particulate matters (PM) as particulate substances contained in exhaust gas. A particulate matter sensor 8 (a PM sensor) is installed in the exhaust passage 4 downstream of the DPF 6. Incidentally, various catalysts for exhaust gas purification and the like as well as the DPF 6 are installed in the exhaust passage 4 of the internal combustion engine 2, but the description thereof is omitted herein.

This system includes a control apparatus 10. Various sensors of the internal combustion engine 2 as well as the PM sensor 8 are connected to an input side of the control apparatus 10. Besides, an electric circuit for the PM sensor 8 of the internal combustion engine 2 and various other actuators are connected to an output side of the control apparatus 10. The control apparatus 10 executes a predetermined program on the basis of information input from the various sensors, and operates the various actuators and the like to perform various kinds of control regarding the operation of the internal combustion engine 2.

Figure 2:
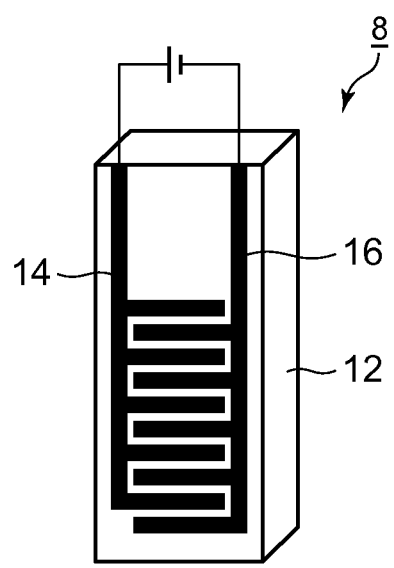
FIG. 2 is a schematic view for illustrating a configuration of an element portion of a PM sensor of each embodiment of the invention.

FIG. 2 is a schematic view for illustrating the configuration of an element portion of the PM sensor 8 of the first embodiment of the invention. As shown in FIG. 2, the element portion of the PM sensor 8 includes an insulating substrate 12. A pair of electrodes 14 and 16 are formed on a surface of the insulating substrate 12. The pair of the electrodes 14 and 16 are arranged spaced apart from each other by a certain clearance and out of contact with each other. The electrodes 14 and 16 have regions formed like a comb tooth, and are formed in such a manner as to mesh with each other in these regions. Incidentally, electrodes 20 and 22 having a comb tooth shape are exemplified in this first embodiment of the invention. However, the invention is not limited to such a shape, and it is sufficient that a pair of electrodes be opposed to each other. A heater (not shown) is embedded in a layer below the electrodes 14 and 16 inside the insulating substrate 12.

The pair of the electrodes 14 and 16 are connected to an electric power supply (not shown) via an electric circuit or the like. Thus, a high voltage is applied between the electrode 14 and the electrode 16. Besides, the heater is connected to the electric power supply (not shown) via the electric circuit or the like. Thus, the heater is supplied with a predetermined electric power, and the element portion is heated as a result. This electric power supply is controlled by the control apparatus 10.

[Outline of Control in this First Embodiment]

The control that is performed by the control apparatus 10 in this first embodiment of the invention includes the control of detection of a PM amount, the control of the resetting of the PM sensor 8, and the control of a determination on a malfunction in the DPF 6 as will be described below.

(1) Detection of PM Amount

In detecting a PM discharge amount, "a collection voltage" as a high voltage for collecting PM is applied between the electrodes 14 and 16. If the collection voltage is applied between the electrodes 14 and 16, the PM in exhaust gas is collected and deposited between the electrodes 14 and 16. As the amount of the PM deposited between the electrodes 14 and 16 increases, the number of conduction locations between the electrodes 14 and 16 increases, and the resistance value between the electrodes 14 and 16 becomes small. That is, the resistance value between the electrodes 14 and 16 of the PM sensor 8 is correlated with the amount of the PM deposited on the electrodes 14 and 16.

In the first embodiment of the invention, an electrical characteristic that is correlated with the resistance between the electrodes 14 and 16 is detected as an output of the PM sensor 8. An amount of the PM deposited between the electrodes 14 and 16 is detected on the basis of an output of this PM sensor 8 (hereinafter referred to also as "a sensor output"). The amount of the PM deposited on the electrodes 14 and 16 changes in an interlocking manner as the amount of the PM contained in exhaust gas changes. Accordingly, the amount of PM is used as an index of the PM discharged downstream of the DPF 6.

Incidentally, in the following embodiments of the invention, for descriptive purposes, the electrical characteristic detected as the sensor output will be described as a value that increases as the amount of the PM between the electrodes 14 and 16 increases. However, in the invention, the PM sensor is not limited to this. On the contrary, it is also possible to employ a sensor that outputs an electrical characteristic that decreases as the amount of PM increases. Besides, in the following embodiments of the invention, an amount of PM detected on the basis of a sensor output is referred to also as "a first PM amount" (a first particulate matter amount).

(2) PM Reset (Removal Treatment of Particulate Matters)

The sensor output increases as the amount of the PM deposited between the electrodes 14 and 16 increases. However, when the amount of deposition between the electrodes 14 and 16 reaches a limit value, the sensor output does not change any more. In this state, the PM sensor 8 cannot issue an output corresponding to the amount of the PM in exhaust gas. Accordingly, at a predetermined timing, the PM deposited on the element portion needs to be removed once. A treatment of removing this PM is referred to also as "PM reset".

In PM reset, the control apparatus 10 supplies the heater of the PM sensor 8 with a predetermined electric power, and superheats the element portion of the PM sensor 8 such that the temperature thereof rises to a temperature at which PM is removed through combustion. Thus, the PM adherent to the element portion of the PM sensor 8 is removed through combustion. Incidentally, it should be noted herein that the temperature of the element portion during a PM reset period is higher than 500° C., more preferably, higher than 700° C. Alternatively, it is also appropriate to set a target temperature of the element portion during the PM reset period higher than 500° C., more preferably, higher than 700° C., and supply the heater with electric power. The temperature at which PM burns is about 500 to 650° C. Therefore, if the reset temperature is set equal to or higher than 700° C. (preferably 700 to 800° C.), the certainty with which PM burns can be enhanced.

Incidentally, the PM deposited on the element portion of the PM sensor 8 is removed through this PM reset. Therefore, PM reset is carried out at various timings, for example, before or after the start of a determination on a malfunction in the DPF 6 as will be described below, after a regeneration treatment of the DPF 6 for removing, through combustion, the PM that has adhered onto the DPF 6, etc.

(3) Determination on Malfunction in DPF (Determination on Presence or Absence of Malfunction in Particulate Matter Collection Filter)

If the DPF 6 malfunctions, the discharge amount of the PM passing through the DPF 6 and discharged downstream of the DPF 6 increases. Accordingly, in the case where the DPF 6 malfunctions, the deposition amount of the PM deposited between the electrodes 14 and 16 of the PM sensor 8 gradually increases, and the sensor output increases correspondingly. Accordingly, a determination on the malfunction in the DPF 6 can be made on the basis of the sensor output.

Concretely, in making a determination on a malfunction in the DPF 6 according to this first embodiment of the invention, the control apparatus 10 carries out PM reset to remove the PM deposited on the element portion, and then starts applying a collection voltage to the PM sensor 8 in this state. The control apparatus 10 detects a sensor output at a timing (a detection timing) when an integrated value (an estimated discharge amount) of the amount of the PM estimated to have been discharged from the internal combustion engine 2 reaches a reference discharge amount REF_1. The control apparatus 10 compares the detected sensor output with a reference output REF_2 as a criterion for determination. If the sensor output is larger than the reference output REF_2, it is determined that there is a malfunction in the DPF 6.

Incidentally, the estimated discharge amount is calculated according to a predetermined model, using, for example, an engine rotational speed, a torque, EGR and the like of the internal combustion engine 2 as parameters. The reference discharge amount REF_1 is set to an amount at which the PM needed to issue an output corresponding to the amount of PM is deposited and which is sufficient to determine whether or not there is a malfunction in the DPF 6. The reference discharge amount REF_1 is stored in advance in the control apparatus 10. Besides, the reference output REF_2 as a criterion for determining whether or not there is a malfunction is set to a suitable value by causing the sensor output corresponding to the integrated value of the amount of the PM discharged downstream of the DPF 6, which is permitted in the case where the DPF 6 is normal, to include a permissible error or the like, etc. This reference output REF_2 is stored in advance in the control apparatus 10.

[Confirmation Control of Output of PM Sensor in this First Embodiment]

By the way, the resistance between the electrodes 14 and 16 may change through the use of the PM sensor 8. Concretely, for example, the resistance value between the electrodes 14 and 16 may become high due to decreases in areas of the electrodes 14 and 16 resulting from evaporation of the electrodes 14 and 16. Besides, the resistance value between the electrodes 14 and 16 may become high due to the adhesion of insulating materials such as Ash and the like to the electrodes 14 and 16 as well. On the contrary, the resistance value between the electrodes 14 and 16 may also become low due to a narrowed clearance between the electrodes 14 and 16 resulting from migration.

In the case where the resistance value between the electrodes 14 and 16 thus changes, the correlation between the sensor output and the amount of PM breaks, so that the amount of PM cannot be accurately detected. As a result, a deterioration in the accuracy of the control based on the sensor output, such as an erroneous determination on a malfunction in the DPF 6 or the like, may be incurred. Accordingly, in this first embodiment of the invention, the following confirmation control is performed in order to confirm whether or not the sensor output is properly output.

Figure 3:
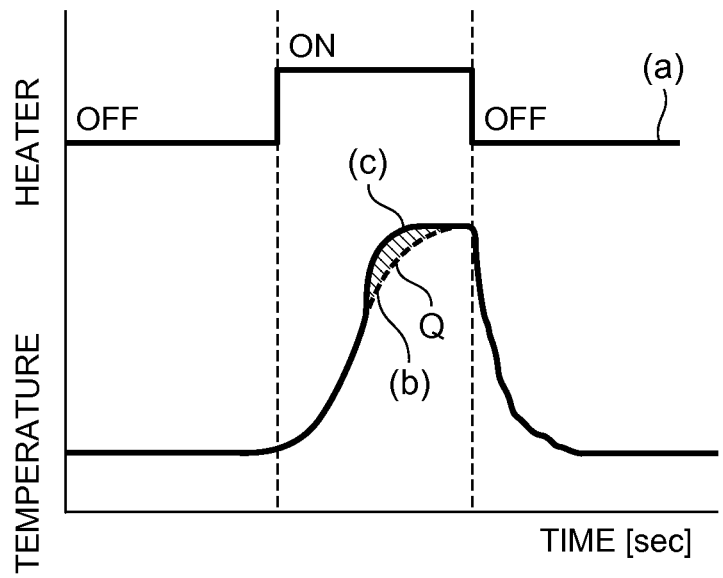
FIG. 3 is a view for illustrating by comparison changes in temperature of the element portion during PM reset in a case where PM is deposited and a case where no PM is deposited.

FIG. 3 is a view for illustrating changes in the temperature of the element portion during PM reset in the first embodiment of the invention. In FIG. 3, the axis of abscissa represents time, and the axis of ordinate represents the ON/OFF state of the heater or the temperature of the element portion. Besides, in FIG. 3, a solid line (a) represents the ON/OFF state of the heater, a curve (b) represents a profile of changes in the temperature of the element portion in the case where no PM is deposited, and a curve (c) represents changes in the temperature of the element portion in the case where PM is deposited.

As shown in FIG. 3, when the heater is turned ON to start PM reset, the temperature of the element portion of the PM sensor 8 on which PM is deposited (see the curve (c)) rises to become higher than the temperature of the element portion of the PM sensor 8 on which no PM is deposited (see the curve (b)). This difference between the temperatures of the element portion results from the generation of heat through the combustion of PM during PM reset. That is, a heat generation amount Q that causes a change in temperature that does not result from the heating by the heater is considered to be correlated with the amount of the PM adherent to the element portion immediately before the start of PM reset.

Figure 4:
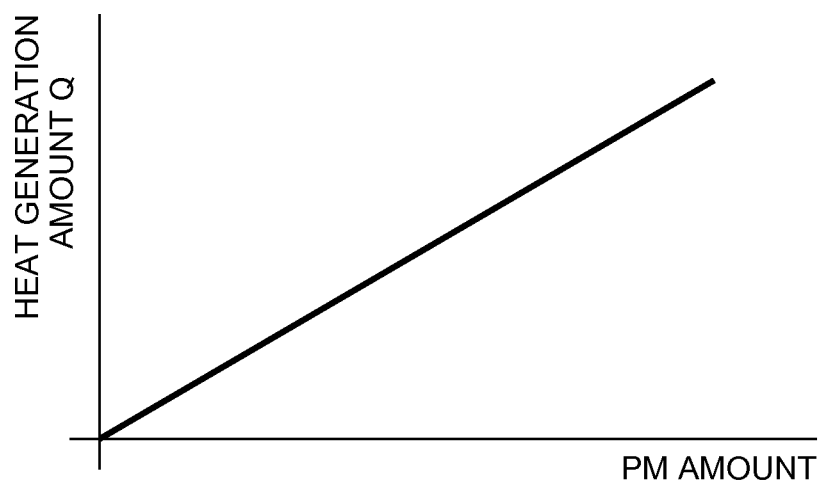
FIG. 4 is a view for illustrating a relationship between a heat generation amount of the element portion of the PM sensor and an amount of deposited PM in the first embodiment of the invention.

FIG. 4 is a view for illustrating a relationship between the amount of the PM deposited on the element portion of the PM sensor 8 and the heat generation amount Q during PM reset.

In FIG. 4, the axis of abscissa represents the amount of PM, and the axis of ordinate represents the heat generation amount Q. As shown in FIG. 4, the heat generation amount Q of the element portion during PM reset increases substantially in proportion to the amount of the deposited PM. On the basis of this relationship, in this first embodiment of the invention, the heat generation amount Q is detected, and the amount of the PM deposited before PM reset is detected on the basis of the heat generation amount Q. Incidentally, in this first embodiment of the invention, the amount of PM detected on the basis of the heat generation amount Q is referred to also as "a second PM amount".

The heat generation amount Q during PM reset can be detected by monitoring a change in the temperature of the element portion during PM reset and subtracting a change in temperature resulting from the heating by the heater (a temperature of the element portion in the case where no PM has adhered) from the detected change in the temperature of the element portion (see "Q" of FIG. 3). Incidentally, the change in the temperature of the element portion can be obtained by, for example, detecting a change in the resistance of the heater. Alternatively, it is also possible to install a temperature sensor in the vicinity of the element portion, and detect a temperature of the element portion on the basis of an output of the temperature sensor.

In this first embodiment of the invention, PM reset is carried out under a condition that satisfies (Condition 1) to (Condition 4) mentioned below, in order to accurately detect the heat generation amount Q and the second PM amount based thereon.

(Condition 1) PM reset is carried out with a larger amount of PM deposited on the element portion than during conventional PM reset. This is intended to clarify a difference between a change in the temperature of the element portion resulting from the generation of heat through the combustion of PM and a change in the temperature resulting the heating of the element portion by the heater, and to more accurately detect the heat generation amount Q.

Concretely, in this first embodiment of the invention, PM reset is started as soon as the sensor output reaches a start output REF_3 after the completion of a determination on a malfunction in the DPF 6. Thus, PM reset can be carried out with a larger amount of PM adherent to the element portion.

Incidentally, the time of PM reset is set longer by a length corresponding to an increase in the adhesion amount of PM in comparison with conventional cases. Thus, PM is reliably removed after the completion of PM reset. The start output REF_3 is a value that is at least larger than the reference output REF_2, is set in accordance with an amount of PM needed to more accurately detect the heat generation amount Q, and is stored in advance in the control apparatus 10.

(Condition 2) PM reset is carried out under an operating condition that the temperature of exhaust gas be lower than a reference temperature REF_4. In this first embodiment of the invention, the heat generation amount Q is detected in accordance with the change in the temperature of the element portion during PM reset. It should be noted herein that the change in the temperature of the element portion through the combustion of PM is more accurately detected in the case where the temperature of an environment around the PM sensor 8 is low to a certain extent. Accordingly, in order to more accurately detect the heat generation amount Q, PM reset is carried out under the operating condition that the temperature of exhaust gas be lower than the reference temperature REF_4. The reference temperature REF_4 is set to a value close to an upper limit of a temperature range that can ensure the accuracy of changes in temperature through the combustion of PM. Such a value is a value that is obtained in advance through an experiment or the like, and is stored in the control apparatus 10.

(Condition 3) PM reset is carried out under an operating condition that an estimated instantaneous discharge amount as a discharge amount of PM per unit time during PM reset be small. This is because if the amount of discharged PM becomes large, the heat generation amount Q is considered to change due to the adhesion of the PM discharged during PM reset.

Concretely, a determination is made depending on whether or not the estimated instantaneous discharge amount is smaller than a reference amount REF_5. The reference amount REF_5 mentioned herein is set to a value close to an upper limit of a range of the estimated instantaneous discharge amount in which the influence on the change in the temperature of the element portion during PM reset is permissible. The reference amount REF_5 is a value that is obtained through an experiment or the like for each PM sensor, and is stored in advance in the control apparatus 10.

(Condition 4) PM reset is carried out under an operating condition that the recirculation of exhaust gas by an EGR system be stopped (EGR be suspended) and the amount of change in accelerator opening degree be limited. In a state where EGR is ON or the amount of change in accelerator opening degree is large, a large amount of PM is discharged from the internal combustion engine 2. Accordingly, in order to restrain the discharge amount of PM during PM reset from increasing, EGR is suspended, and the amount of change in accelerator opening degree is limited such that the accelerator opening degree gently changes, during PM reset.

By the way, in the case where the PM sensor 8 is normal, a first PM amount XS that is obtained on the basis of a sensor output immediately before the start of PM reset theoretically coincides with a second PM amount XQ that is obtained on the basis of the heat generation amount Q during PM reset.

In this first embodiment of the invention, with the aid of this theoretical fact, the control of confirming the PM sensor 8 is performed. Concretely, a sensor output is detected at a detection timing immediately before the start of PM reset, and the first PM amount XS is obtained on the basis of this sensor output. On the other hand, the heat generation amount Q during PM reset that is carried out under a condition satisfying the aforementioned (Condition 1) to (Condition 4) is detected, and the second PM amount XQ is obtained on the basis of this heat generation amount Q.

After that, a difference between the first PM amount XS and the second PM amount XQ is obtained, and it is determined whether the PM sensor 8 is normal or abnormal, depending on whether or not this difference between the PM amounts is larger than a reference value REF_6. Incidentally, the reference value REF_6 is set to a value close to an upper limit of a range in which it can be determined that the first PM amount XS and the second PM amount XQ substantially coincide with each other in consideration of ranges of permissible errors and the like of both the values (XS, XQ). This value is stored in advance in the control apparatus 10.

Figure 5:
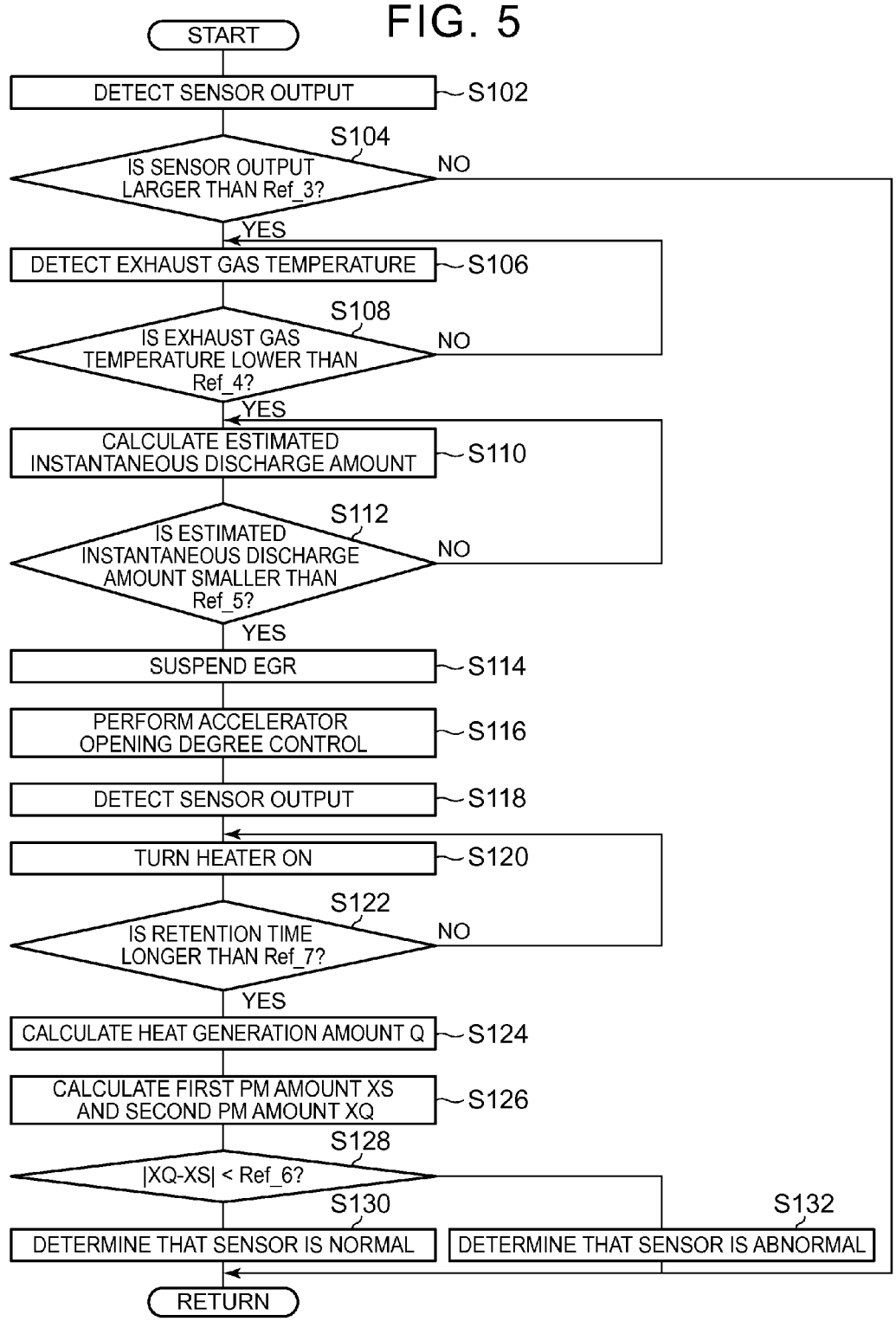
FIG. 5 is a flowchart for illustrating a routine of control that is performed by a control apparatus in the first embodiment of the invention.

FIG. 5 is a flowchart for illustrating a routine of the control performed by the control apparatus 10 in the first embodiment of the invention. The routine of FIG. 5 is repeatedly executed at intervals of a certain time during the operation of the internal combustion engine 2. In FIG. 5, first of all, a sensor output is detected (S102).

Subsequently, it is determined whether or not the detected sensor output is larger than the start output REF_3 (S104). In this step, it is determined whether or not PM is deposited to such an extent that the heat generation amount Q resulting from the combustion of PM can be more or less accurately detected. A concrete value of the start output REF_3 is stored in advance in the control apparatus 10. It should be noted herein that if a relationship: the sensor output>the start output REF_3 is not recognized to be fulfilled, the present processing temporarily ends. After that, this routine is started again from step S102.

On the other hand, if the relationship: the sensor output>the start output REF_3 is recognized to be fulfilled in step S104, an exhaust gas temperature is then detected (S106). The exhaust gas temperature is detected on the basis of, for example, an output of a temperature sensor (not shown) that is installed in the exhaust passage 4.

Subsequently, it is determined whether or not the exhaust gas temperature is lower than the reference temperature REF_4 (S108). In this step, it is determined whether or not the temperature of exhaust gas around the PM sensor 8 is low enough to more or less accurately detect a change in the temperature of the element portion. Incidentally, the concrete reference temperature REF_4 is a value that is stored in advance in the control apparatus.

If a relationship: the exhaust gas temperature<the reference temperature REF_4 is not recognized to be fulfilled in step S108, a return is made to step S106 to detect an exhaust gas temperature again. That is, in step S108, the detection of the exhaust gas temperature and the determination on the fulfillment of the relationship: the exhaust gas temperature<the reference temperature REF_4 are repeated until an environment in which the exhaust gas temperature is lower than the reference temperature REF_4 is recognized to have arisen.

If the relationship: the exhaust gas temperature<the reference temperature REF_4 is recognized to be fulfilled in step S108, an estimated instantaneous discharge amount is then calculated (S110). The estimated instantaneous discharge amount is a value that is calculated according to a model using the engine rotational speed, the torque and the like as parameters, in accordance with a current operating state. The estimated instantaneous discharge amount is an amount of the PM discharged per unit time as predicted in the current operating state.

Subsequently, it is determined whether or not the estimated instantaneous discharge amount is smaller than a reference amount REF_5 (S112). In this step, it is determined whether or not the influence of the estimated instantaneous discharge amount of the discharged PM on the detection of the heat generation amount Q is within a permissible range. The concrete reference amount REF_5 is a value that is stored in advance in the control apparatus 10.

If the relationship: the estimated instantaneous discharge amount<the reference amount REF_5 is not recognized to be fulfilled in step S112, a return is made again to step S110 to calculate a current estimated instantaneous discharge amount. After that, it is determined whether or not a relationship: the estimated instantaneous discharge amount<the reference amount REF_5 is fulfilled (S112). That is, the calculation of the estimated instantaneous discharge amount in step S110 and the subsequent determination process in step S112 are repeatedly carried out until the estimated instantaneous discharge amount is recognized to have become smaller than the reference amount REF_5 in step S112.

On the other hand, if the relationship: the estimated instantaneous discharge amount<the reference amount REF_5 is recognized to be fulfilled in step S112, EGR is then suspended (S114). Thus, the recirculation by the EGR system is controlled to a stopped state.

Subsequently, the amount of change in the accelerator opening degree of the internal combustion engine 2 is limited (S116). Although the accelerator opening degree is controlled according to another control program, the amount of change in the accelerator opening degree in that control is limited to a predetermined range in this step. Thus, the discharge amount of PM is restrained from increasing due to a sudden change in the accelerator opening degree.

Subsequently, a sensor output is detected (S118). Subsequently, the heater is turned ON (S120). Thus, PM reset is started. Subsequently, it is determined whether or not a retention time since the turning ON of the heater has become longer than a reference time REF_7 (S122). In this step, it is determined whether or not a time sufficient to remove, through combustion, the PM adherent to the element portion has elapsed. The concrete reference time is stored in advance in the control apparatus 10.

If a relationship: the retention time>the reference time REF_7 is not recognized to be fulfilled in step S122, the determination on the relationship: the retention time>the reference time REF_7 in step S122 is repeated. That is, the determination in step S122 is repeatedly made with the heater kept ON, until the retention time reaches the reference time REF_7.

If the relationship: the retention time>the reference time REF_7 is recognized to be fulfilled in step S122, the heat generation amount Q is then calculated (S124). The heat generation amount Q is detected on the basis of a difference in temperature between a profile of the change in the temperature of the element portion since the turning ON of the heater in step S120 and a profile of a reference change in temperature. The profile of the reference change in temperature is a change in the temperature of the element portion in the case where the heater is turned ON with no PM deposited, and is stored in advance in the control apparatus 10.

Subsequently, the first PM amount XS and the second PM amount XQ are obtained (S126). The first PM amount XS is obtained in accordance with the sensor output detected in step S118. On the other hand, the second PM amount XQ is obtained in accordance with the heat generation amount Q detected in step 124. Incidentally, a relationship between the heat generation amount Q and the second PM amount XQ is calculated on the basis of a map or the like that is stored in advance in the control apparatus 10.

Subsequently, it is determined whether or not an absolute value of a difference between the first PM amount XS and the second PM amount XQ, which are calculated in step S126, is smaller than a reference value REF_6 (S128). The reference value REF_6 is a reference value for determining whether or not there is a malfunction in the PM sensor 8, and is stored in advance in the control apparatus 10.

If the difference |XS−XQ| between the PM amounts is recognized to be smaller than the reference value REF_6 in step S128, it is determined that the PM sensor 8 is normal (S130). On the other hand, if the difference |XS−XQ| between the PM amounts is not recognized to be smaller than the reference value REF_6 in step S128, it is determined that the PM sensor 8 is abnormal (S132). After the determination in step S130 or S132, the present processing is ended. Incidentally, if it is determined in step S132 that the PM sensor 8 is abnormal, predetermined control, for example, the display of a warning lamp, the prohibition of a determination on a malfunction in the DPF 6 based on the PM sensor 8, or the like is performed.

As described above, in this first embodiment of the invention, the PM amount is detected on the basis of the heat generation amount Q during PM reset and thus can be compared with the PM amount based on the output of the PM sensor 8. Thus, it can be confirmed whether the PM sensor 8 is normal or abnormal. Thus, the confirmation of, for example, a determination on a malfunction in the DPF 6 or the like, which is based on the output of the PM sensor 8, can be carried out. Accordingly, an erroneous determination based on the sensor output in the case where there is a malfunction in the PM sensor 8 can be prevented.

Incidentally, the case where the suspension of EGR (S114) and the limitation of the amount of change in the accelerator opening degree (S116) are carried out to restrain the discharge amount of PM from increasing has been described. However, the invention is not limited to this case. For example, it is acceptable to carry out only one of the suspension of EGR and the limitation of the accelerator opening degree.

Besides, in this first embodiment of the invention, the case where PM reset at the time of detection of the heat generation amount Q is carried out in a state satisfying all the aforementioned conditions, namely, (Condition 1) to (Condition 4) has been described. This is intended to detect the second PM amount XQ based on the heat generation amount Q as accurately as possible, and to accurately determine whether or not there is a malfunction in the PM sensor 8. In this invention, however, the detection of the heat generation amount Q is not limited to cases where all the aforementioned conditions, namely, (Condition 1) to (Condition 4) are satisfied. Only one or a plurality of (Condition 1) to (Condition 4) may be satisfied, or these conditions may not be set. The contents of the conditions should not be limited to those of (Condition 1) to (Condition 4). Other conditions for enhancing the detectability of the heat generation amount Q may be set. This holds true for the following embodiment of the invention as well.

Besides, in this first embodiment of the invention, the condition that the sensor output be larger than the start output REF_3 is set as the condition for PM reset in the case where the heat generation amount Q is detected (Condition 1). However, this invention is not limited to this condition. For example, the reference discharge amount REF_1 for making a determination on the timing for detecting the sensor output in making a determination on a malfunction in the DPF 6 may be set larger than a normal value. Thus, the time for the determination on a malfunction in the DPF 6 becomes long, and a larger amount of PM can be deposited at the time of the start of PM reset. Besides, it is also appropriate to start PM reset as soon as a predetermined time elapses after the completion of the determination on a malfunction in the DPF 6, and set this predetermined time definitely longer than in the case of the normal start of PM reset. This holds true for the following embodiment of the invention as well.

Besides, in this first embodiment of the invention, the case where it is determined whether or not there is a malfunction in the DPF 6, on the basis of the sensor output in the case where the estimated discharge amount has become larger than the reference discharge amount REF_1 has been described. In this invention, however, the method of making a determination on a malfunction in the DPF 6 is not limited to this method. For example, it is also appropriate to detect a sensor output as soon as a predetermined time elapses after the completion of detection of a malfunction in the DPF 6, and determine, on the basis of this sensor output, whether or not there is a malfunction in the DPF 6. In this case, in detecting the heat generation amount Q during PM reset, a large amount of PM may be allowed to be deposited by further setting "the predetermined time" longer than usual. Incidentally, in this case as well, the amount of the PM adherent to the element portion is larger than in conventional cases. However, the large amount of the adherent PM is removed by setting the time for PM reset long. This holds true for the following embodiment of the invention as well.

Besides, in this first embodiment of the invention, the case where it is determined whether or not the PM sensor 8 is normal, on the basis of whether or not the absolute value |XS−XQ| of the difference between the first PM amount XS and the second PM amount XQ is smaller than the reference value REF_6 has been described. However, this invention is not limited to this case. It may also be confirmed whether or not the PM sensor 8 is normal, according to another method of comparing the first PM amount XS and the second PM amount XQ with each other. Concretely, it is also appropriate to detect a discrepancy between the first PM amount XS and the second PM amount XQ, for example, a difference therebetween, a ratio therebetween or the like, and confirm, on the basis of this discrepancy, whether or not the PM sensor 8 is normal. Besides, it is also appropriate to detect the first PM amount XS and the second PM amount XQ a plurality of times, obtain averages of the respective amounts, then detect a discrepancy therebetween, and confirm whether or not the PM sensor 8 is normal. This holds true for the following embodiment of the invention as well.

Second Embodiment

A system of the second embodiment of the invention has a configuration similar to that of the system of the first embodiment of the invention. In the system of the second embodiment of the invention, due to control similar to that of the first embodiment of the invention, the control for using the PM sensor 8 even if it is determined that the PM sensor 8 is abnormal is performed.

Figure 6:
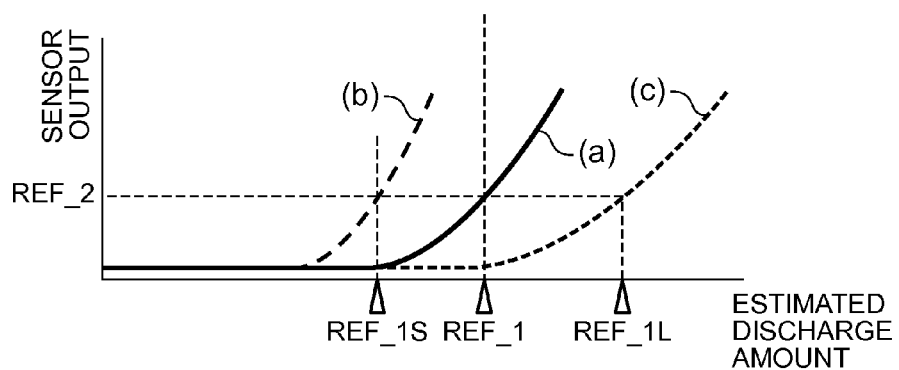
FIG. 6 is a view for illustrating control in the second embodiment of the invention.

FIG. 6 is a view for illustrating a relationship between an estimated discharge amount and a sensor output in this second embodiment of the invention. In FIG. 6, the axis of abscissa represents the estimated discharge amount of PM, and the axis of ordinate represents the sensor output. Besides, in FIG. 6, a curve (a) represents a normal sensor output, a curve (b) represents a sensor output in the case of enhanced sensitivity, and a curve (c) represents a sensor output in the case of lowered sensitivity.

In the second embodiment of the invention, the second PM amount XQ calculated from the heat generation amount Q is used as an amount matching the amount of the PM actually deposited on the element portion. Then, if the first PM amount XS is larger than the second PM amount XQ, the resistance value between the electrodes 14 and 16 themselves is considered to be small due to a cause such as a narrowed clearance between the electrode 14 and the electrode 16 or the like as a result of, for example, migration of the electrodes 14 and 16. In this case, it is determined that there is established a state where the sensitivity of the PM sensor 8 is enhanced and the PM sensor 8 issues an output larger than an actual amount of PM.

In this case, as indicated by the curve (b) of FIG. 6, for example, in a normal determination on a malfunction in the DPF 6, the sensor output for the reference discharge amount REF_1 as a timing for detecting the sensor output is larger than in the case where the PM sensor 8 is normal. That is, in a determination on a malfunction in the DPF 6, in the case where it is determined, through a comparison between the sensor output and the reference output REF_2, whether or not there is a malfunction in the DPF 6, the time for the determination needs to be advanced. Accordingly, in the determination on a malfunction in the DPF 6, a reference value that determines a timing for detecting a sensor output is defined as a reference discharge amount REF_1S that is smaller than the reference discharge amount REF_1 in the case where the PM sensor 8 is normal. Thus, in the case where the sensitivity of the PM sensor 8 is enhanced, the detection of the sensor output in the determination on a malfunction in the DPF 6 is carried out at an early timing when the estimated discharge amount has reached the reference discharge amount REF_1S.

On the other hand, if the first PM amount XS is smaller than the second PM amount XQ, the resistance between the electrodes 14 and 16 is considered to be large due to, for example, a cause such as evaporation of the electrodes 14 and 16, adhesion of insulating materials to the electrodes 14 and 16 or the like. In this case, it is determined that there is established a state where the sensitivity of the PM sensor 8 is lowered and the PM sensor 8 issues an output smaller than an actual amount of PM.

In the case where the sensitivity of the sensor output is lowered, as indicated by the curve (c) of FIG. 6, for example, the sensor output for the reference discharge amount REF_1 is lower than in the case where the PM sensor 8 is normal. That is, in making a determination on a malfunction in the DPF 6, in order to determine, through a comparison between the sensor output and the reference output REF_2, whether or not there is a malfunction in the DPF 6, the time for the determination needs to be retarded. Accordingly, in making a determination on a malfunction in the DPF 6, a reference value that determines a timing for detecting a sensor output is defined as a reference discharge amount REF_1L that is larger than the reference discharge amount REF1 in the case where the PM sensor 8 is normal. Thus, in the case where the sensitivity of the PM sensor 8 is lowered, the detection of the sensor output in making a determination on a malfunction in the DPF 6 is carried out at a late timing when the estimated discharge amount has reached the reference discharge amount REF_1L.

Incidentally, suitable values are obtained and set as the small reference discharge amount REF_1S in the case where the sensitivity of the PM sensor 8 is enhanced and the large reference discharge amount REF_1L in the case where the sensitivity is lowered, through an experiment or the like for the respective cases. These values are stored in advance in the control apparatus 10 together with the reference discharge amount REF_1 during normal operation.

Figure 7:
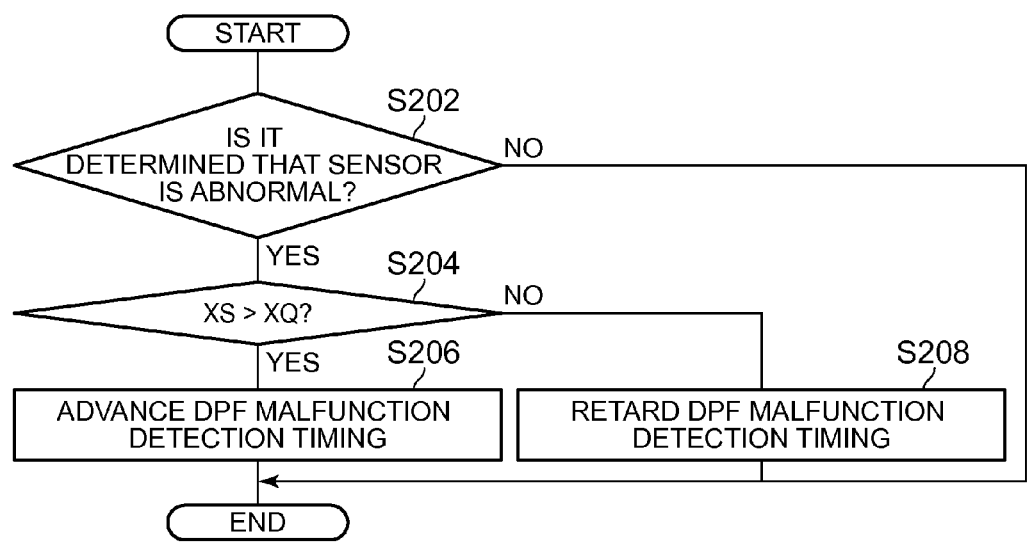
FIG. 7 is a flowchart for illustrating a routine of control that is performed by a control apparatus in the second embodiment of the invention.

FIG. 7 is a flowchart for illustrating a routine of the control performed by the control apparatus 10 in the second embodiment of this invention. The routine of FIG. 7 is subsequently executed after a determination on the normality/abnormality of the sensor in the routine of FIG. 5. In the routine of FIG. 7, first of all, it is determined whether or not it is determined that the PM sensor 8 is abnormal (S202). If it is not recognized that it is determined that the PM sensor 8 is abnormal, the present processing ends.

On the other hand, if it is recognized in step S202 that it is determined that the PM sensor 8 is abnormal, it is then determined whether or not the first PM amount XS is larger than the second PM amount XQ (S204). If a relationship: the first PM amount XS>the second PM amount XQ is recognized to be fulfilled in step S204, the sensitivity of the PM sensor 8 is considered to be enhanced. Accordingly, in this case, the timing for making a determination on a malfunction in the DPF 6 is advanced (S206). Concretely, the reference discharge amount in making a determination on a malfunction in the DPF 6 is set to the reference discharge amount REF_1S that assumes a value smaller than usual. Incidentally, the changed reference discharge amount REF_1S is stored in advance in the control apparatus 10. After that, the present processing ends.

On the other hand, if the relationship: the first PM amount XS>the second PM amount XQ is not recognized to be fulfilled in step 204, the sensor sensitivity of the PM sensor 8 is considered to be lowered. Accordingly, in this case, the timing for making a determination on a malfunction in the DPF 6 is retarded (S208). Concretely, the reference discharge amount in making a determination on a malfunction in the DPF 6 is set to the reference discharge amount REF_1L that assumes a value larger than usual. The reference discharge amount REF_1L changed herein is stored in advance in the control apparatus 10. After that, the present processing ends.

As described above, according to this second embodiment of the invention, the timing for making a determination on a malfunction can be changed in accordance with a change in the sensitivity of the PM sensor 8, even in the case where there is an abnormality in the sensitivity of the sensor output. Thus, even in the case where there is a deviation in the output of the PM sensor 8, the deviation can be corrected, and a determination on a malfunction in the DPF 6 can be continuously made more or less accurately.

Incidentally, in this second embodiment of the invention, the case where a change in the sensitivity of the PM sensor 8 is coped with by changing the reference discharge amount as a criterion for making a determination on the timing for detecting a sensor output in making a determination on a malfunction in the DPF 6 has been described. However, this invention is not limited to this case. For example, it is also appropriate to refrain from changing the timing for making a determination on a malfunction in the DPF 6, and change the magnitude of a collection voltage applied between the electrodes 14 and 16 during a determination on a malfunction in the DPF 6. Concretely, the change in the sensitivity of the PM sensor 8 can be coped with by setting the applied voltage high if it is determined that the sensitivity of the PM sensor 8 is lowered (i.e., XS<XQ), and setting the applied voltage low if it is determined that the sensitivity is enhanced (i.e., XS>XQ).

Besides, in the invention, a determination on a malfunction in the DPF 6 may be made by, for example, detecting a sensor output after the lapse of a predetermined time since the start of application of the collection voltage, and determining, on the basis of this sensor output, whether or not there is a malfunction. In this case, furthermore, this "predetermined time" can be set long if it is determined that the sensitivity of the PM sensor 8 is lowered, and "the predetermined time" can be set short if the sensitivity is enhanced.

Besides, in this second embodiment of the invention, the case where the timing for detecting a sensor output in making a determination on a malfunction is uniformly (e.g., REF_1S or REF_1L) changed for each of the case where the sensitivity is lowered and the case where the sensitivity is enhanced when the PM sensor 8 is normal while the timing is changed in accordance with a change in the sensitivity of the PM sensor 8 has been described. However, this invention is not limited to this case. For example, it is also appropriate to change stepwise the timing for detecting a sensor output in accordance with the magnitude of a deviation in sensitivity. For example, it is also acceptable to use a difference XS−XQ between the first PM amount XS and the second PM amount XQ as a parameter, and gradually change, either stepwise or steplessly, the reference discharge amount, the predetermined time or the applied voltage for determining the aforementioned malfunction detection timing, in accordance with this difference.

Besides, in this second embodiment of the invention, the case where the detection timing is changed in accordance with the change in sensitivity according to steps S204 to S208 of FIG. 7 if there is an abnormality after it is determined whether or not there is an abnormality in the PM sensor 8 in steps S128 to S132 in the routine of FIG. 5 has been described. However, this invention may also be designed to perform only a process of changing the detection timing in accordance with a difference between the first PM amount XS and the second PM amount XQ, without determining whether or not the PM sensor 8 is abnormal. Concretely, this process can be realized by, for example, executing the steps to S126 in the routine of FIG. 5, detecting the first PM amount XS and the second PM amount XQ, and subsequently performing the processes of steps S204 to S208 of FIG. 7 to change the detection timing.

In the case where the numerical values such as the number, quantity, amount, range and the like of the respective elements are mentioned in each of the foregoing embodiments of the invention, this invention is not limited to the mentioned numerical values, unless they are specified in particular or specifically designated as those obvious in principle. Besides, the structure, manufacturing process and the like described in each of these embodiments of the invention are not indispensable for this invention unless they are specified in particular or specifically designated as those obvious in principle.

DESCRIPTION OF REFERENCE SYMBOLS

2 INTERNAL COMBUSTION ENGINE
4 EXHAUST PASSAGE
6 DPF (PARTICULATE MATTER COLLECTION FILTER)
8 PM SENSOR (PARTICULATE MATTER SENSOR)
10 CONTROL APPARATUS
12 INSULATING SUBSTRATE
14, 16 ELECTRODE
Q HEAT GENERATION AMOUNT
XS FIRST PM AMOUNT (FIRST PARTICULATE MATTER AMOUNT)
XQ SECOND PM AMOUNT (SECOND PARTICULATE MATTER AMOUNT)
REF_1, REF_1S, REF_1L REFERENCE DISCHARGE AMOUNT
REF_2 REFERENCE OUTPUT
REF_3 START OUTPUT
REF_4 REFERENCE TEMPERATURE
REF_5 REFERENCE AMOUNT
REF_6 REFERENCE VALUE
REF_7 REFERENCE TIME

The invention claimed is:

1. A control apparatus for an internal combustion engine, comprising a controller configured to:
    carry out a removal treatment of removing, through combustion, particulate matters deposited on an element portion of a particulate matter sensor that is arranged in an exhaust passage of the internal combustion engine, by raising a temperature of the element portion;
    detect a first particulate matter amount as an amount of particulate matters, which are deposited on the element portion of the particulate matter sensor before start of the removal treatment, on a basis of an output of the particulate matter sensor before start of the removal treatment;
    detect a heat generation amount that results from combustion of the particulate matters during the removal treatment;
    detect a second particulate matter amount as an amount of particulate matters, which are deposited on the element portion before start of the removal treatment, in accordance with the heat generation amount; and
    determine whether or not there is an abnormality in the particulate matter sensor, on a basis of a difference between the first particulate matter amount detected and the second particulate matter amount,
    wherein the controller is configured to prohibit start of the removal treatment until the amount of particulate matters deposited on the element portion reaches a reference amount, wherein the reference amount in a case where the controller determines whether or not there is an abnormality in the particulate matter sensor is larger than a reference amount of particulate matters in other cases.

2. The control apparatus for the internal combustion engine according to claim 1, wherein:
    a particulate matter collection filter for collecting the particulate matters is arranged in the exhaust passage upstream of the particulate matter sensor;
    the controller is configured to determine, on a basis of an output of the particulate matter sensor, whether or not there is a malfunction in the particulate matter collection filter, and set a detection timing for detecting an output of the particulate matter sensor, for determining whether or not there is a malfunction in the particulate matter collection filter; and
    the controller is configured to set the detection timing later than a detection timing in a case where it is determined that the particulate matter sensor is normal, if it is determined that the particulate matter sensor is abnormal and the first particulate matter amount is smaller than the second particulate matter amount, and set the detection timing earlier than the detection timing in the case where it is determined that the particulate matter sensor is normal, if it is determined that the particulate matter sensor is abnormal and the first particulate matter amount is larger than the second particulate matter amount.

3. The control apparatus for the internal combustion engine according to claim 1, wherein:
    a particulate matter collection filter for collecting the particulate matters is arranged in the exhaust passage upstream of the particulate matter sensor;
    the controller is configured to determine, on a basis of an output of the particulate matter sensor, whether or not there is a malfunction in the particulate matter collection filter, and set a magnitude of a particulate matter collection voltage that is applied to the particulate matter sensor, in determining whether or not there is a malfunction in the particulate matter collection filter; and
    the controller is configured to set the particulate matter collection voltage larger than a particulate matter collection voltage that is applied in a case where it is determined that the particulate matter sensor is normal, if it is determined that the particulate matter sensor is abnormal and the first particulate matter amount is smaller than the second particulate matter amount, and sets the particulate matter collection voltage smaller than the particulate matter collection voltage that is applied in the case where it is determined that the particulate matter sensor is normal, if it is determined that the particulate matter sensor is abnormal and the first particulate matter amount is larger than the second particulate matter amount.

4. A control method for an internal combustion engine, comprising:
    carrying out a removal treatment of removing, through combustion, particulate matters deposited on an element portion of a particulate matter sensor that is arranged in an exhaust passage of the internal combustion engine, by raising a temperature of the element portion;

detecting a first particulate matter amount as an amount of particulate matters, which are deposited on the element portion of the particulate matter sensor before start of the removal treatment, on a basis of an output of the particulate matter sensor before start of the removal treatment;

detecting a heat generation amount that results from combustion of the particulate matters during the removal treatment;

detecting a second particulate matter amount as an amount of particulate matters, which are deposited on the element portion before start of the removal treatment, in accordance with the heat generation amount; and determining whether or not there is an abnormality in the particulate matter sensor, on a basis of a difference between the first particulate matter amount and the second particulate matter amount, wherein start of the removal treatment is prohibited until the amount of particulate matters deposited on the element portion reaches a reference amount wherein the reference amount in a case where the controller determines whether or not there is an abnormality in the particulate matter sensor is larger than a reference amount of particulate matters in other cases.

5. The control method for the internal combustion engine according to claim 4, wherein start of the removal treatment is prohibited until a temperature of exhaust gas of the internal combustion engine becomes lower than a reference temperature.

6. The control method for the internal combustion engine according to claim 4, further comprising:

determining, on a basis of an output of the particulate matter sensor, whether or not there is a malfunction in a particulate matter collection filter for collecting the particulate matters, wherein:

the particulate matter collection filter is arranged in the exhaust passage upstream of the particulate matter sensor; and a detection timing for detecting an output of the particulate matter sensor for determining whether or not there is a malfunction in the particulate matter collection filter is set later than a detection timing in a case where it is determined that the particulate matter sensor is normal, if it is determined that the particulate matter sensor is abnormal and the first particulate matter amount is smaller than the second particulate matter amount, and is set earlier than the detection timing in the case where it is determined that the particulate matter sensor is normal, if it is determined that the particulate matter sensor is abnormal and the first particulate matter amount is larger than the second particulate matter amount.

7. The control method for the internal combustion engine according to claim 4, further comprising:

determining, on a basis of an output of the particulate matter sensor, whether or not there is a malfunction in a particulate matter collection filter for collecting the particulate matters, wherein the particulate matter collection filter is arranged in the exhaust passage upstream of the particulate matter sensor; and a magnitude of a particulate matter collection voltage that is applied to the particulate matter sensor in determining whether or not there is a malfunction in the particulate matter collection filter is set larger than a particulate matter collection voltage that is applied in a case where it is determined that the particulate matter sensor is normal, if it is determined that the particulate matter sensor is abnormal and the first particulate matter amount is smaller than the second particulate matter amount, and is set smaller than the particulate matter collection voltage that is applied in the case where it is determined that the particulate matter sensor is normal, if it is determined that the particulate matter sensor is abnormal and the first particulate matter amount is larger than the second particulate matter amount.

\* \* \* \* \*